United States Patent [19]

Qualeatti et al.

[11] 4,410,460
[45] * Oct. 18, 1983

[54] PROCESS FOR THE REDUCTION OF UNSATURATED CARBOXYLIC ACIDS

[75] Inventors: Gail M. Qualeatti, Palatine; Dalia Germanas, Des Plaines, both of Ill.

[73] Assignee: UOP Inc., Des Plaines, Ill.

[*] Notice: The portion of the term of this patent subsequent to Jul. 20, 1999 has been disclaimed.

[21] Appl. No.: 329,357

[22] Filed: Dec. 9, 1981

[51] Int. Cl.$^3$ .................................................. C11C 3/12
[52] U.S. Cl. ..................................... 260/409; 260/410; 260/410.9 R; 260/410.9 N; 560/205; 560/225; 568/885
[58] Field of Search .................. 260/410.9 N, 410.9 R, 260/410.9 D, 410, 409; 560/205; 568/885

[56] References Cited
U.S. PATENT DOCUMENTS 3,361,776 1/1968 De Vries ..................... 260/410.9 D
3,595,816 7/1971 Barrett ................................. 260/409
4,117,242 9/1978 Fozzard .............................. 260/409
4,124,617 11/1968 Knifton ............................... 260/410
4,340,546 7/1982 Qualeatti et al. ..................... 260/409

Primary Examiner—Helen M. S. Sneed
Attorney, Agent, or Firm—James R. Hoatson, Jr.; Raymond H. Nelson; William H. Page, II

[57] ABSTRACT

Unsaturated carboxylic acids may be reduced to an ester or to a corresponding alcohol by treatment with hydrogen in the presence of a reducing catalyst system. The reducing catalyst system which is used in the present invention comprises rhenium and a nitrogen-containing compound composited on a solid support as exemplified by rhenium and ammonium hydroxide composited on gamma-alumina. By utilizing this catalyst system, it is possible to obtain products in which the carbonyl group of the molecule has been reduced with some retention of the double bond of the carbon chain.

13 Claims, No Drawings

PROCESS FOR THE REDUCTION OF UNSATURATED CARBOXYLIC ACIDS

BACKGROUND OF THE INVENTION

It is known that unsaturated carboxylic acids may be reduced to an ester or to the corresponding alcohol. However, the reducing catalysts which have heretofore been employed are not selective in the hydrogenation process, and thus the reductive process usually results in eliminating the retention of the unsaturation in the carbon chain. The compound which is obtained is therefore a saturated ester or alcohol. This is true when utilizing catalysts such as a mixture of copper and chromium oxide or rhenium catalysts which may be used in either a supported or unsupported state or which may also contain a noble metal of Group VIII of the Periodic Table, such as platinum, palladium or ruthenium.

In many instances, it is desirable to retain the unsaturation of the carbon chain when obtaining either alcohols or esters of the starting unsaturated carboxylic acid. As will hereinafter be shown in greater detail, it has now been discovered that a process for effecting the reduction of unsaturated carboxylic acids may be effected by utilizing certain catalytic compositions of matter and also by utilizing certain modifications of the process to obtain esters or alcohols of unsaturated carboxylic acids in which the double bonds present in the original acid are retained in the reaction product to a greater extent than without the catalyst and process modifications.

BRIEF SUMMARY OF THE INVENTION

This invention relates to a process for the reduction of unsaturated carboxylic acids. More specifically, the invention is concerned with a process for treating unsaturated carboxylic acids of the type hereinafter set forth in greater detail to effect a reduction of said acids in which the unsaturated bonds which are present in the original acid are retained in the product.

Unsaturated acid esters, or alcohols, especially those which possess a relatively long carbon atom chain, will find a wide variety of uses in the chemical field. The unsaturated acid esters as exemplified by oleyl oleate may be used as a substitute for sperm whale oil which is becoming increasingly difficult to obtain. Sperm whale oil is used as a high grade lubricating oil for light machinery such as watches, clocks and scientific instruments as well as in heat-treating and rustproofing. In addition to use as a lubricant, the esters which are obtained according to the process of this invention may also be used in cosmetics such as perfumes, colognes, bath oils, soaps, powders, etc. This is especially true in the case of relatively long chain unsaturated esters.

It is therefore an object of this invention to provide a process for the reduction of unsaturated carboxylic acids.

A further object of this invention is to provide a process for the reduction of an unsaturated carboxylic acid whereby the ester and/or alcohol product resulting from the process will retain the unsaturation of the starting material.

In one aspect, an embodiment of this invention resides in a process for the reduction of an unsaturated carboxylic acid which comprises treating said acid in a reaction system in the presence of hydrogen and a reducing catalyst comprising rhenium and a nitrogen-containing compound composited on a solid support at treatment conditions, and recovering the resultant unsaturated product.

A specific embodiment of this invention is found in the process for the reduction of an unsaturated carboxylic acid which comprises treating oleic acid in a reaction system in the presence of hydrogen and a reduction catalyst system comprising a rhenium-containing compound and ammonium hydroxide composited on a solid support at a temperature in the range of from about 100° to about 500° C. and a pressure in the range of from about 100 to about 5000 pounds per square inch (psi), continuously bleeding hydrogen from said reaction system during the reaction period, and recovering the resultant oleyl oleate, oleyl alcohol and/or their geometric and positional isomers.

Other objects and embodiments can be found in the following further detailed description of the present invention.

As hereinbefore set forth, the present invention is concerned with a process for the reduction of an unsaturated carboxylic acid in which said acid is treated with hydrogen in the presence of a reduction catalyst system of the type hereinafter set forth in greater detail. By employing this catalyst system, and also by employing certain reaction conditions, it is possible to obtain the resulting ester and/or alcohol in which the unsaturation in the carbon atom chain which is present in the starting material will be retained to a greater degree than is possible when utilizing other catalysts. In addition, by effecting a hydrogen bleed during the reaction, the product water which is formed during the reaction is continuously removed, thus permitting an enhanced activity and selectivity of the reaction to form the desired products.

Examples of unsaturated carboxylic acids which may be employed as starting materials to form the desired unsaturated esters will include those acids containing from 3 to about 22 carbon atoms, some specific examples of these acids being acrylic acids; the isomeric butenic acids such as crotonic acid, isocrotonic acid, vinyl acetic acid, methylacrylic acid; the isomeric pentenic acids such as tiglic acid, angelic acid, senecioic acid; the isomeric hexenoic acids; heptenoic acids; octenoic acids; nonenoic acids; decenoic acids; undecenoic acids; dodecenoic acids; tridecenoic acids; tetradecenoic acids; pentadecenoic acids; hexadecenoic acids such as hypogeic acid; heptadecenoic acids; octadecenoic acids such as oleic acid, elaidic acid; nonadecenoic acids; eicosenoic acids; erucic acid; brassidic acid, etc. It is to be understood that the aforementioned unsaturated carboxylic acids are only representative of the type of compound which may be employed to form the desired esters, and that the present invention is not necessarily limited thereto.

The catalyst system which is employed to effect the reduction of the aforesaid acids while retaining the unsaturation of the carbon chain to a greater degree than was heretofore possible will be a catalytic composite comprising a rhenium compound composited on a solid support and a nitrogen-containing compound. The rhenium will be present on the solid support in a low valence oxidation state, usually in the form of rhenium oxide or metallic rhenium in an amount in the range of from about 0.1 to about 2% by weight of the composite. Examples of rhenium compounds which may be employed to form the desired catalyst will include rhenium trichloride, rhenium pentachloride, rhenium oxide, perrhenic acid, etc. The aforementioned rhenium compounds will be composited on a solid support which, in the preferred embodiment of the invention, comprises a relatively high surface area inorganic oxide. Examples of these inorganic oxides will include aluminas such as gamma-alumina, eta-alumina, theta-alumina, silica or mixtures of inorganic oxides such as alumina-silica, silica-zirconia, silica magnesia, alumina-silica-zirconia, etc.

Examples of nitrogen-containing compounds which are present in the catalyst system preferably in an amount in the range of from about 0.1 to about 10% by weight of the catalyst will include ammonia, ammonium hydroxide, primary alkyl amines such as methylamine, ethylamine, propylamine, isopropylamine, n-butylamine, the isomeric pentylamines, hexylamines, heptylamines, octylamines, nonylamines, decylamines, etc; secondary amines such as dimethylamine, diethylamine, dipropylamine, diisopropylamine, di-n-butylamine, the isomeric dipentylamines, dihexylamines, diheptylamines, dioctylamines, dinonylamines, didecylamines, etc; tertiary amines such as trimethylamine, triethylamine, tripropylamine, triisopropylamine, tri-n-butylamine, the isomeric tripentylamines, trihexylamines, triheptylamines, trioctylamines, trinonylamines, tridecylamines;, etc; arylamines such as aniline, diphenylamine triphenylamine, N-benzylamine, N,N-dibenzylamine, o-tolylamine, m-tolylamine, p-tolylamine, etc; heterocyclic amines such as pyrole, pyrazole, triazole, pyridine, pyridazine, pyrimidine, pyrazine, piperazine, triazine, etc. It is to be understood that the aforementioned nitrogen-containing compounds are only representative of the class of nitrogen-containing compounds which may be employed in the catalyst system and that the use of said compounds will not necessarily give equivalent results.

The reduction catalysts which are used in the process of the present invention may be prepared in any suitable manner. For example, one type of preparation which may be used comprises impregnating a solid support such as gamma-alumina with an aqueous solution of a rhenium compound such as perrhenic acid for a period of time which is sufficient to allow the deposition of the desired amount of rhenium on the solid support, that is, an amount sufficient so that the finished catalyst composite will contain from about 0.1 to about 2% of rhenium. Following this, the nitrogen-containing compound may then be utilized to impregnate the catalyst composite under similar conditions so that the finished catalyst system will contain the amine in the desired amount, that is, from about 0.1 to about 10% of the amine. Alternatively, a coimpregnation may be effected in which the solid support is coimpregnated with the rhenium compound and the nitrogen-containing compound for a period of time sufficient to deposit the desired amount of both rhenium and nitrogen compounds on the base. After recovery of the impregnated solid support, the composite is then calcined at a temperature which may range from about 250° to about 750° C. in an air atmosphere for a period of time which may range from about 0.5 hour up to about 4 hours in duration. Following this, if so desired, the calcined composite may then be subjected to a reducing treatment by heating the composite at a temperature within the range hereinbefore set forth, that is, from about 250° to about 750° C. in a hydrogen atmosphere for a period of time sufficient to reduce the rhenium to a low valence oxidation state.

It is also contemplated that the catalyst which is used in the process of the present invention may be prepared in a continuous manner of operation. When such a type of operation is employed, the solid support material comprising an inorganic oxide of the type hereinbefore set forth in greater detail which may be of any desired shape such as pellets, spheres, globules, rods, etc. is continuously passed through an aqueous solution of a rhenium-containing compound at a predetermined rate of speed in order that the predetermined amount of rhenium may be impregnated on the support. The support, after passage through the solution, is continuously withdrawn and passed to a calcination zone wherein it is treated at an elevated temperature, in the presence of air, within the range hereinbefore set forth. After completion of the calcination period, the rhenium-impregnated material is then passed through a second impregnation bath comprising a solution of a nitrogen-containing compound. Alternatively, it is also contemplated that the rhenium and the nitrogen-containing compound may be coimpregnated on the solid support in a single impregnation zone following which the impregnated solid support is calcined and thereafter, if so desired, subjected to a reducing step in which the impregnated support is continuously passed through a reducing zone at an elevated temperature while being subjected to a hydrogen flow. Following the reduction, the composite is continuously withdrawn and recovered.

The reduction process of the present invention which results in the obtention of esters and alcohols which still possess the unsaturation of the starting materials and which are recovered in an amount greater than that which was hereinbefore obtained may be effected in either a batch or continuous type operation. When utilizing a batch type operation, a quantity of the unsaturated carboxylic acid, which is used to undergo esterification or to obtain an alcohol, is placed in an appropriate apparatus which is pressure-resistant in nature, such as an autoclave of the rotating, mixing or stirring type. In addition, the particular catalyst hereinbefore described is also added to the apparatus in an amount in the range of from about 25:1 to about 5:1 grams of acid per gram of catalyst. After pressuring the apparatus to an initial operating pressure, the apparatus is then heated to the desired operating temperature and maintained thereat for a predetermined period of time. The operating conditions which are employed to effect the desired reduction process will include a temperature in the range of from about 100° to about 500° C. and superatmospheric pressures ranging from about 100 to about 5000 psi for a period of time which may range from about 0.5 up to about 10 hours or more in duration, the reaction time being determined by the particular unsaturated carboxylic acid undergoing reduction as well as the reaction temperature and amount of pressure which is employed during the reaction. The superatmospheric pressures which are employed may be afforded by hydrogen alone or, if so desired, the amount of hydrogen present may afford only a partial pressure, the remainder of the desired operating pressure being afforded by the presence of an inert gas such as nitrogen, helium, argon, etc. in the reaction apparatus. During the reaction period, a predetermined amount of hydrogen is continuously bled from the reaction vessel, the water which is formed as a side product during the reaction being removed along with the hydrogen. The amount of hydrogen which is bled from the reaction appartus will be dependent upon the amount charged, said amount which is recovered being sufficient enough to maintain the desired operating pressure at a predetermined level. Upon completion of the desired reaction period, the hydrogen charge is discontinued as is the heat treatment, and after the reaction vessel or apparatus has returned to room temperature, the excess pressure is discharged, the apparatus is opened, and the reaction mixture is recovered therefrom. The thus recovered mixture may then be filtered to separate the catalyst system from the reaction product, the latter then being subjected to conventional means of separation to recover the desired ester and/or alcohol.

It is also contemplated within the scope of this invention that the reduction process may be effected in a continuous manner of operation. When such a type of operation is employed, a reaction vessel containing the reduction catalyst system is maintained at the proper operating conditions of temperature and pressure, the unsaturated carboxylic acid which is to undergo reduction is continuously charged to the reaction vessel where it is contacted with the catalyst system in the presence of hydrogen which is also continuously charged to the reactor. After passage through the reaction vessel for a predetermined period of time, the reactor effluent is continuously withdrawn from the reaction vessel and subjected to conventional means of separation whereby the desired ester or alcohol of the unsaturated carboxylic acid which still possesses the unsaturation of the starting material, is separated and recovered, while any unreacted starting materials, both gaseous and liquid in nature, after being dried to remove the water formed during the reaction, are recycled to the reaction vessel to form a portion of the feedstock.

It is contemplated that the continuous method of operation may be effected in various ways. For example, the reduction catalyst may be positioned in the reaction vessel as a fixed bed, and the unsaturated carboxylic acid undergoing reduction is passed over the bed in either an upward or downward flow. Another method of effecting the reaction is to employ the catalyst system as a moving bed in the reaction vessel and having the unsaturated carboxylic acid and the catalyst system pass through the reaction vessel either concurrently or countercurrently to each other. Likewise, if so desired, a slurry-type of operation may be employed in which the reduction catalyst system is carried into the reaction vessel as a slurry in the unsaturated carboxylic acid.

The following examples are given for purposes of illustrating the process of the present invention utilizing the particular reducing catalyst system. However, it is to be understood that these examples are given merely for purposes of illustration and that the present invention is not necessarily limited thereto.

EXAMPLE I

In this example, a catalyst was prepared by impregnating 125 grams of alumina with 250 grams of an aqueous perrhenic acid solution to afford a 1% rhenium-to-base ratio. The impregnation was allowed to proceed for a period of 4 hours following which the impregnated alumina was recovered, calcined at a temperature of 500° C. in an air atmosphere for a period of 1 hour and thereafter reduced in a hydrogen atmosphere at a temperature of 500° C. for an additional period of 2 hours. A feedstock comprising 200 grams of oleic acid and 10 grams of the catalyst, prepared according to the above paragraph, was charged to a 1 liter stirred autoclave which was then sealed and flushed twice with hydrogen. The autoclave was then pressured to 100 psi with hydrogen and heated to a temperature of 300° C. Upon reaching the desired operating temperature, the autoclave was further pressured to 1000 psi with hydrogen and the reaction was allowed to proceed for a period of 4 hours while maintaining the temperature at about 300° C., the pressure at 1000 psi, and stirring the autoclave at a rate of 1100 rpm. At the end of the 4 hour period, heating was discontinued and after the autoclave had returned to room temperature the excess pressure was discharged and the autoclave was opened. The reaction mixture which was recovered from the autoclave was filtered to remove the catalyst, and analyzed. Analysis of the product by means of Acid Value and Iodine Value disclosed that there had been no reduction of the carboxyl moiety, but there had been a 13% reduction of the double bond.

EXAMPLE II

To illustrate the ability of the catalyst system of the present invention to afford a reduction of the carboxyl moiety, a second catalyst was prepared by impregnating 150 grams of gamma-alumina with 300 cc of an aqueous perrhenic acid solution containing an excess of ammonium hydroxide sufficient to form ammonium perrhenate in situ. The impregnation was allowed to proceed for a period of 4 hours following which the impregnated alumina base containing 1% rhenium-to-base ratio was recovered. The composite was calcined at a temperature of 600° C. for a period of 1 hour in an air atmosphere.

As in Example I above, 200 grams of oleic acid and 10 grams of the catalyst system prepared according to the above paragraph were charged to a 1 liter stirred autoclave. The autoclave was flushed with hydrogen, sealed and pressured to 100 psi with hydrogen. The autoclave was then heated to a temperature of 310° C., further pressured with hydrogen to 1000 psi and stirred at a rate of 1100 rpm for a period of 4 hours. At the end of the 4 hour period, heating was discontinued and, after the autoclave had returned to room temperature, the excess pressure was vented and the autoclave was opened. The reaction product was recovered, filtered to remove the catalyst and analyzed. Analysis of the product disclosed that there had been a 45% reduction of the carboxyl moieties to predominantly esters and alcohols including oleyl oleate, oleyl alcohol, as well as geometric and positional isomers thereof with a 25% reduction or saturation of the double bond.

EXAMPLE III

In a similar manner, 125 grams of gamma-alumina were impregnated with an aqueous ammonium perrhenate solution sufficient to afford a 1% rhenium-to-base ratio. After impregnation had proceeded for a period of 4 hours, the composite was recovered, calcined at a temperature of 500° C. in an air atmosphere for a period of 1 hour, followed by reduction by hydrogen at a temperature of 500° C. for a period of 1 hour.

As in the preceeding examples, 200 grams of oleic acid and 10 grams of the catalyst system prepared according to the above paragraph were treated in a manner similar to that set forth in Example I above, that is, by reaction at a temperature of 300° C. and a pressure of 1000 psi of hydrogen for a period of 4 hours. After the 4 hour reaction period had elapsed, heating was discontinued, the autoclave was allowed to return to room temperature, and the excess pressure was vented. Analysis of the reaction product after separation from the catalyst disclosed that there had been a 94% reduction of the carboxyl moieties to form oleyl oleate, oleyl alcohol as well as geometric and positional isomers thereof with an 83% reduction of the double bond.

EXAMPLE IV

Two hundred grams of oleic acid and 10 grams of the catalyst system prepared in Example III were reacted at a temperature of 300° C. and a pressure of 1000 psi of hydrogen while stirring the autoclave at 1100 rpm. In addition, hydrogen was bled from the reaction vessel at a rate of 1 cubic foot per hour, while admitting sufficient hydrogen to maintain the desired operating pressure. After 2 hours, the reaction product recovered from the autoclave showed 82% reduction of the carboxyl moiety with 36% reduction of olefinic bonds.

EXAMPLE V

In this example, gamma-alumina was activated by subjecting the alumina to a stream of air at a temperature of 500° C. Following this, ammonia gas was passed over the activated base for a period of 18 hours. The base was then impregnated with an aqueous ammonium perrhenate solution in a steam drier so that the catalyst composite contained a 1% rhenium-to-base ratio. The composite was then calcined in an air atmosphere at a temperature of 500° C. for a period of 1 hour and thereafter reduced in a hydrogen atmosphere at a temperature of 500° C. for an additional period of 1.5 hours.

As in the above examples, 200 grams of oleic acid and 10 grams of catalyst were reacted at a temperature of 300° C., and a pressure of 1000 psi of hydrogen for a period of 4 hours, while stirring the autoclave at 1100 rpm. After recovery of the reaction product from the autoclave, analysis disclosed that there had been a 92% reduction of the carboxyl moiety with a corresponding 77% reduction of the double bond.

EXAMPLE VI

As a further illustration of the ability of a nitrogen-containing compound to selectively reduce the carboxyl moiety of an unsaturated acid, a catalyst was prepared by impregnating gamma-alumina with an aqueous perrhenic acid solution containing 1% rhenium-to-base ratio in a steam drier. The resulting impregnated alumina was calcined in air for a period of 1 hour at a temperature of 500° C. Thereafter, the composite was reduced in a hydrogen atmosphere at a temperature of 500° C. for a period of 2 hours.

The reduction of an unsaturated acid was accomplished by placing 200 grams of oleic acid, 10 grams of a catalyst prepared according to the above paragraph, and 2 grams pyridine in a stirred autoclave. Reaction conditions which were employed were similar in nature to those set forth in the above examples, that is, the autoclave was stirred at a rate of 1100 rpm for a period of 4 hours while maintaining a temperature of 300° C. and a hydrogen pressure of 1000 psi. After completion of the reaction period, the product was recovered and analyzed. Analysis of the product disclosed that there had been a 9% reduction of the carboxyl moiety to esters and alcohols with a 20% reduction or saturation of the double bond. This reduction, both of the carboxyl moiety and the double bond, is in contradistinction to prior statements as set forth in the *Journal of Organic Chemistry*, September 1963, pages 2347 to 2350, that saturation of olefinic bonds in carbonyl compounds does not occur when catalysts are poisoned by the presence of a nitrogen-containing compound such as pyridine.

EXAMPLE VII

In a manner similar to that hereinbefore set forth, the treatment of other unsaturated acids such as hypogeic acid, erucic acid, crotonic acid, hexenoic acid, utilizing a catalyst system comprising rhenium and a nitrogen-containing compound composited on a support such as alumina and utilizing reaction conditions similar to those hereinbefore set forth of temperature, hydrogen pressure and time, may result in the production of unsaturated esters and alcohols such as hypogeyl hypogeate, hypogeyl alcohol, erucyl erucate, erucyl alcohol, crotonyl crotonate, crotonyl alcohol, hexenyl hexenate, hexenyl alcohol, as well as geometric and positional isomers thereof.

We claim as our invention:

1. A process for the reduction of an unsaturated carboxylic acid which comprises treating said acid in a reaction system in the presence of hydrogen and a reducing catalyst comprising from about 0.1 to about 2% by weight rhenium and from about 0.1 to about 10.0% by weight of said rhenium of a nitrogen-containing compound composited on a solid support, wherein said nitrogen-containing compound is selected from the group consisting of ammonia, ammonium hydroxide, a primary alkylamine, a secondary dialkyl amine, a tertiary trialkyl amine, an arylamine and a heterocyclic amine at treatment conditions, and recovering the resultant unsaturated alcohol, ester or alcohol and ester reaction product.

2. The process as set forth in claim 1 in which said treatment conditions include a temperature in the range of from about 100° to about 500° C. and a pressure in the range of from about 100 to about 5000 psi.

3. The process as set forth in claim 1 further characterized in that hydrogen is continuously bled from said reaction system.

4. The process as set forth in claim 1 in which said solid support comprises a high surface area alumina.

5. The process as set forth in claim 4 in which said high surface area alumina is gamma-alumina.

6. The process as set forth in claim 1 in which said tertiary trialkyl amine is trimethylamine.

7. The process as set forth in claim 1 in which said secondary dialkyl amine is diethylamine.

8. The process as set forth in claim 1 in which said heterocyclic amine is pyridine.

9. The process as set forth in claim 1 in which said unsaturated acid is oleic acid and said unsaturated product is a mixture of oleyl oleate, oleyl alcohol and geometric and positional isomers thereof.

10. The process as set forth in claim 1 in which said unsaturated acid is hypogeic acid and said unsaturated product is a mixture of hypogeyl hypogeate, hypogeyl alcohol, and geometric and positional isomers thereof.

11. The process as set forth in claim 1 in which said unsaturated acid is erucic acid and said unsaturated product is a mixture of erucyl erucate, erucyl alcohol and geometric and positional isomers thereof.

12. The process as set forth in claim 1 in which said unsaturated acid is crotonic acid and said unsaturated product is a mixture of crotonyl crotonate and crotonyl alcohol.

13. The process as set forth in claim 1 in which said unsaturated acid is hexenoic acid and said unsaturated product is a mixture of hexenyl hexenate and hexenyl alcohol.

* * * * *